(12) United States Patent
Park et al.

(10) Patent No.: US 9,039,772 B2
(45) Date of Patent: May 26, 2015

(54) IMAGE-BASED PATIENT-SPECIFIC MEDICAL SPINAL SURGERY METHOD AND SPINAL PROSTHESIS

(75) Inventors: Suk Ho Park, Gwangju (KR); Jong Oh Park, Gyeonggido (KR)

(73) Assignee: INDUSTRY FOUNDATION OF CHONNAM NATIONAL UNIVERSITY, Gwangju (KR)

( * ) Notice: Subject to any disclaimer, the term of this patent is extended or adjusted under 35 U.S.C. 154(b) by 0 days.

(21) Appl. No.: 13/499,612

(22) PCT Filed: Dec. 9, 2009

(86) PCT No.: PCT/KR2009/007262
§ 371 (c)(1),
(2), (4) Date: Mar. 30, 2012

(87) PCT Pub. No.: WO2011/040677
PCT Pub. Date: Apr. 7, 2011

(65) Prior Publication Data
US 2012/0191192 A1    Jul. 26, 2012

(30) Foreign Application Priority Data

Sep. 30, 2009 (KR) .................. 10-2009-0092837

(51) Int. Cl.
*A61F 2/44* (2006.01)
*A61B 17/70* (2006.01)
*A61B 19/00* (2006.01)

(52) U.S. Cl.
CPC .............. *A61B 17/7062* (2013.01); *A61F 2/44* (2013.01); *A61B 17/7065* (2013.01); *A61B 19/5212* (2013.01); *A61B 19/5225* (2013.01)

(58) Field of Classification Search
USPC ............ 623/17.11–17.16, 901; 606/248–249, 606/280–284, 298–299
See application file for complete search history.

(56) References Cited

U.S. PATENT DOCUMENTS

| | | | |
|---|---|---|---|
| 3,648,691 A * | 3/1972 | Lumb et al. .................. 606/279 |
| 6,322,588 B1 * | 11/2001 | Ogle et al. .................... 623/1.46 |
| 7,074,239 B1 * | 7/2006 | Cornwall et al. .......... 623/17.11 |
| 7,567,834 B2 | 7/2009 | Clayton et al. |
| 2006/0036324 A1 * | 2/2006 | Sachs et al. ................ 623/17.11 |
| 2006/0106381 A1 * | 5/2006 | Ferree et al. .................... 606/61 |
| 2006/0106397 A1 | 5/2006 | Lins |
| 2006/0241610 A1 * | 10/2006 | Lim et al. ........................ 606/69 |
| 2007/0118243 A1 * | 5/2007 | Schroeder et al. ............ 700/118 |
| 2007/0168039 A1 | 7/2007 | Trieu |
| 2007/0276501 A1 * | 11/2007 | Betz et al. .................. 623/17.16 |
| 2008/0177326 A1 * | 7/2008 | Thompson .................... 606/277 |
| 2010/0042144 A1 * | 2/2010 | Bennett ......................... 606/213 |

FOREIGN PATENT DOCUMENTS

KR    10-2007-0015153    2/2007

* cited by examiner

*Primary Examiner* — Michael T Schaper
*Assistant Examiner* — Tracy Kamikawa
(74) *Attorney, Agent, or Firm* — Rabin & Berdo, P.C.

(57) ABSTRACT

The present invention relates to an image-based, patient-specific medical spinal surgery technique and to a spinal prosthesis used in the surgery, and particularly, to an image-based, patient-specific medical spinal surgery technique and to a spinal prosthesis which are intended to solve a problem of damage to a spine caused by installing a spinal prosthesis used in spinal surgery, by introducing an image of a patient to manufacture an insertable spinal prosthesis that is customized for a shape of a spine of an individual patient in a polymer-based material.

6 Claims, 7 Drawing Sheets

(a)

(a)

(b)

(b)

(c)

(d)

(a)

(b)

(a)

(b)

(a)

(b)

(a)

(b)

(c)

(d)

IMAGE-BASED PATIENT-SPECIFIC MEDICAL SPINAL SURGERY METHOD AND SPINAL PROSTHESIS

CROSS-REFERENCE TO RELATED APPLICATIONS

This application claims priority under 35 U.S.C. §119 of Korean Patent Application No. 10-2009-0092837, filed on Sep. 30, 2009, the contents of which are hereby incorporated by reference.

BACKGROUND OF THE INVENTION

1. Field of the Invention

The present invention relates to an image-based, patient-specific medical spinal surgery method and a spinal prosthesis for the surgery, and more particularly, to an image-based, patient-specific medical spinal surgery method and a spinal prosthesis for the surgery in which an insertable spinal prosthesis is specified for a shape of each individual patient's spine, is manufactured using a polymer-based material by introducing an image of a patient during surgery, and can be inserted simply during surgery.

2. Description of the Related Art

In treating spine related diseases, an indirect treatment through a physical therapy and a direct treatment to correct and fix a spine by mounting a separate fixing device to a damaged spine are performed.

In other words, the physical therapy is performed when a spinal disease is not serious; however, when a serious disease occurs in a cervical vertebra, a thoracic vertebra, a lumbar vertebra, a sacrum and intervertebral disc, etc., the separate spinal fixing device is used for treatment.

A configuration of the spinal fixing device that is commonly used for a surgery includes a fixing screw that is inserted to a pedicle of a vertebra or a sacral vertebra at a predetermined angle and depth such that a damaged spinal part is corrected to a normal state and fixed in place without moving, a support bar that is positioned on a side of the spinal part, and a fixing cap or a fixing connector for coupling the support bar and the fixing screw.

On the other hand, as shown in FIG. 1, in order to treat the damaged spinal part, the fixing screw is inserted and fixed to the pedicle of the vertebra or the sacral vertebra at an appropriate position and direction, the spinal part is corrected into the normal state by the support bar, and the support bar and the fixing screw are fixed by the fixing cap or the fixing contactor to complete the treatment.

A fixing rod including at least one connecting sliding component that is used for connecting the fixing screw to the fixing rod is inserted to a cylindrical bearing and is fixed by using a tightening means including a small clamp and a tightening screw. The connecting sliding component includes at least one tip that extends away from the cylindrical bearing for the fixing rod in a direction that converges with an axis of the fixing screw. In this manner, the connecting sliding component is temporarily fixed to the spine by being pressed against the spine and the fixing screw is fixed in place by a screw, and lastly, the fixing rod is inserted to the cylindrical bearing in a side direction before fastening the fixing rod by using the small clamp and the fastening screw. The device is designed for spinal transplant on the front.

In a treatment using aforementioned spine fixing device, existing implants are not completely satisfactory. Particularly in the treatment of a spinal bone, the existing implant does not perfectly restore a space between vertebrae, the implant itself becomes an obstacle that hinders the movement of the spine, the implant can be dangerous by being inserted to a vertebral plate, it is difficult to implant the implant, or the implant has a low reliability related to durability of the implant or a transplant fixing unit.

The most serious problem of such a spine fixing device is that the spine fixing device damages the spine.

In a conventional prosthesis for spinal fixation and a surgery using the same, with reference to FIG. 1, the spinal fixation surgery using a screw has the following disadvantages.

First, the prosthesis for correcting the spine is selected based on an image, however the prosthesis is not patient-specific, and a coupling body (e.g., bolt) is nailed into a bone of the spine to attach the spinal prosthesis thereto.

Such invasive spinal treatment may cause a serious problem in that a spinal cord may be damaged and occasionally the bone itself as well.

Also, the spinal prosthesis comprises a relatively large metal structure, by which a patient is repulsed, and the prosthesis that is once adjusted and fixed to the spine is not adjustable such that, when adjustment is required at a later time, an additional surgery is needed.

BRIEF SUMMARY OF THE INVENTION

Therefore, in view of the above-mentioned technical problems and need, the present disclosure provides an image-based, patient-specific medical spinal surgery method and a spinal prosthesis for the surgery in which, in order to solve a problem that a spine may be damaged while mounting a spinal prosthesis being used in the spinal surgery, an image of a patient is introduced to manufacture a polymer material-based spinal prosthesis that is tailored to a shape of a spine of each individual patient and that is insertable to the spine.

The present disclosure also provides an image-based, patient-specific medical spinal surgery method and a spinal prosthesis for the surgery in which an implant prosthesis that is tailored to each individual patient based on an image of a spine produced based on an imaging technique is manufactured.

In addition, in order to overcome a disadvantage that the existing implant is metallic, an implant made of a biocompatible polymer is proposed so that a patient may have less repulsion thereto.

An aspect of the present disclosure provides an image-based, patient-specific medical spinal surgery method comprising: obtaining an image of a spine by using an imaging technique; reconstructing a series of sliced images obtained by the imaging technique into a three dimensional image; extracting respective images of a bone, a muscle, a nerve and so forth from the three dimensional image by using a segmentation technique; analyzing a cause of a disease and planning a treatment thereof based on the extracted three-dimensional image; designing a customized spinal implant prosthesis that conforms to a spine of a patient using the three dimensional image; simulating inserting process of the customized spinal implant prosthesis that conforms to the spine of the patient in the three dimensional image of the spine of the patient prior to performing a surgery; manufacturing the customized spinal implant prosthesis that conforms to the spine of the patient; preparing the surgery on the spine of the patient and implanting the customized spinal prosthesis to a spinal lesion of the patient; activating the inserted customized spinal prosthesis by a body temperature of the patient; and identifying a result of the surgery by obtaining an image of a spinal surgical site of the patient.

Preferably, the imaging technique obtains the image of the spine of the patient through one of a CT, an X-ray, or an MRI.

More preferably, the method further comprises performing a design test of the prosthesis to correct an error between the vertebra and an insert hole of the prosthesis by repeating the simulation of inserting the prosthesis, which is designed to be insertable to a vertebra based on the three dimensional image of the spine of the patient, to the vertebra in the three dimensional image of the spine.

Preferably, the manufacturing of the prosthesis comprises manufacturing the prosthesis in various shapes by directly using a polymer material using a rapid prototyping method.

Preferably, the aforementioned manufacturing of the prosthesis further comprises manufacturing a desired implant prosthesis in a biocompatible polymer using a molding method in which a shape of the implant prosthesis is manufactured using an RP (Rapid Prototyping) polymer and then the prosthesis is molded by the prosthesis mold.

Another aspect of the present disclosure provides an image-based, patient-specific medical spinal prosthesis comprising: a prosthesis that includes a supporting insert hole having a predetermined shape corresponding to a size and a shape of a vertebra of a patient in a surgical site; wherein a plurality of the vertebrae are inserted in the supporting insert hole of the prosthesis corresponding to the vertebra to support between the vertebrae and provide variability such that the prosthesis is modifiable according to movement of a spine.

Preferably, a patient-specific implant prosthesis that is designed so as to be insertable by using a three dimensional image, to support between respective vertebrae of the patient, and to fixedly support the vertebrae that are inserted to the insert holes.

Preferably, the aforementioned prosthesis has a structure preventing from dislocating due to the movement of the spine and is manufactured on the consideration of a load of the spine and hardness of the implant.

More preferably, the aforementioned prosthesis has the insert hole(s) of the prosthesis that is (are) manufactured to have a shape of a reverse phase as the vertebra of the patient such that the prosthesis is insertable to the vertebra based on the three dimensional image of the spine of the patient.

More preferably, the prosthesis is manufactured in a material which expands due to a human body temperature by using a biocompatible polymer material, thereby being more tightly fixed.

According to the present invention, in order to solve a problem that the spine may be damaged while mounting the spinal prosthesis used in the spinal surgery, the image-based patient-specific implant prosthesis is manufactured based on an image of the spine produced by the imaging technique, thereby being tailored to an individual patient.

Also, the screw is not nailed into the spine, thereby achieving a minimally invasive treatment method.

In addition, in order to overcome a disadvantage that the existing implant is metallic, an implant based on the biocompatible polymer is proposed so that the patient may have less repulsion thereto.

Finally, by using a simulation prior to manufacturing the implant, a treatment effect of inserting the prosthesis before/after the surgery may be estimated, and a surgery result may be identified through an image of the surgery.

DESCRIPTION OF REFERENCE NUMBERS FOR MAJOR ELEMENTS OF THE DRAWINGS

Figure 1:
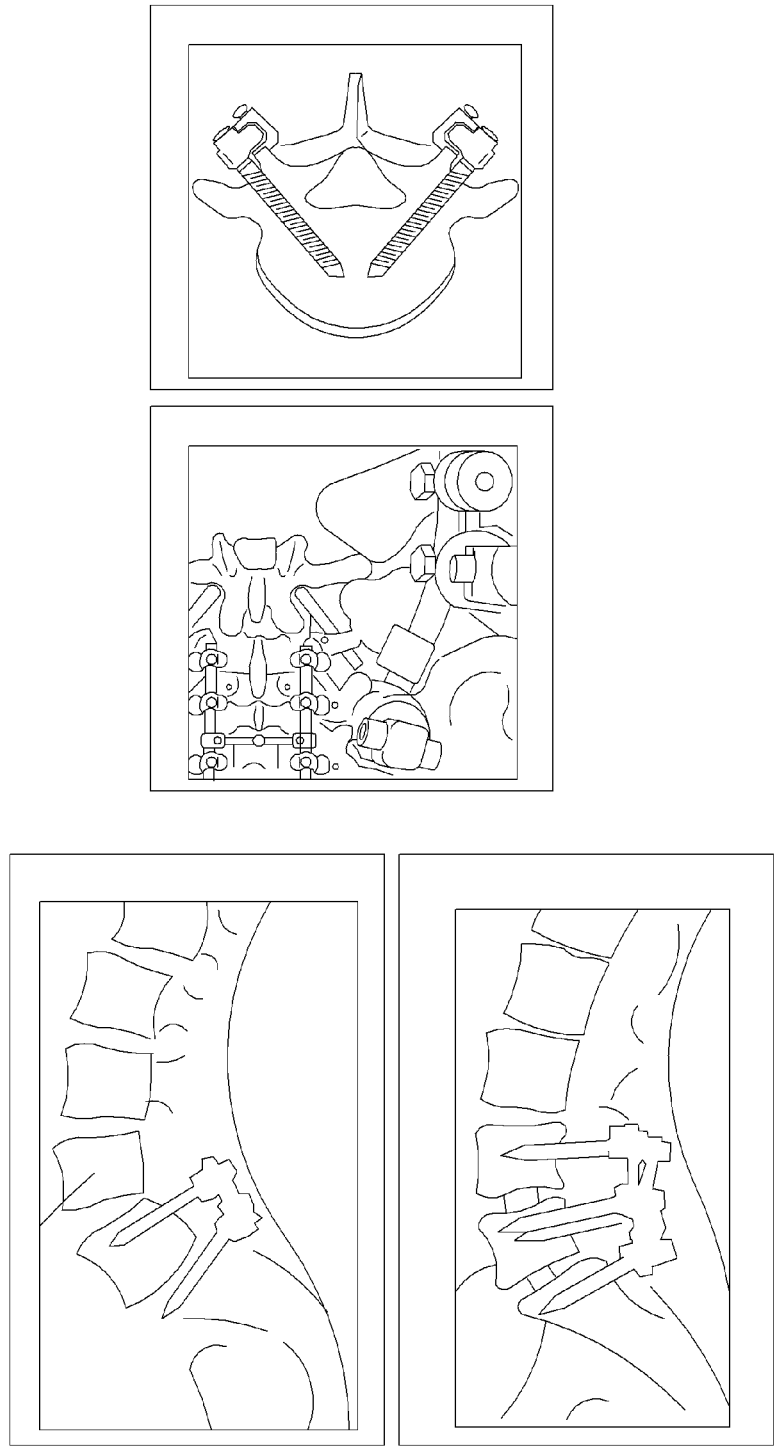
FIG. 1 is a view illustrating a conventional spinal fusion surgery.

10: Spine 20: Vertebral process
200: Prosthesis 210: Insert hole

DETAILED DESCRIPTION OF THE INVENTION

To achieve the above object, the present invention provides an image-based, patient-specific medical spinal surgery method including obtaining an image of a spine by using an imaging technique;

reconstructing a series of sliced images obtained by the imaging technique into a three dimensional image;

extracting respective images of a bone, a muscle, a nerve and so forth from the three dimensional image by using a segmentation technique;

analyzing a cause of a lesion and planning a treatment thereof based on the extracted three-dimensional image;

designing a customized spinal implant prosthesis that conforms to a spine of a patient by using the three dimensional image;

simulating inserting process of the customized spinal implant prosthesis that conforms to the spine of the patient in the three dimensional image of the spine of the patient prior to performing a surgery;

manufacturing the customized spinal implant prosthesis that conforms to the spine of the patient;

preparing the surgery on the spine of the patient and implanting the customized spinal prosthesis to a spinal lesion of the patient;

activating the inserted customized spinal prosthesis by a body temperature of the patient; and identifying a result of the surgery by obtaining an image of a spinal surgical site of the patient.

Hereinafter, exemplary embodiments of the present invention will be described herein below with reference to the accompanying drawings.

Terms or words used in this specification and the claims should not be limitedly interpreted as having common or dictionary meanings, but should be interpreted as having meanings adapted to the technical spirit of the present invention on the basis of a principle that the inventor can appropriately define the concepts of the terms in order to describe his invention in the best way.

Accordingly, the embodiments described in this specification and constructions shown in the drawings illustrate only the most preferred embodiments of the present invention and do not represent the entire technical spirit of the present invention, and therefore, it should be understood that a variety of equivalent arrangements and modifications which may replace the embodiments and the constructions may exist at the time of filing of this application.

Figure 2:
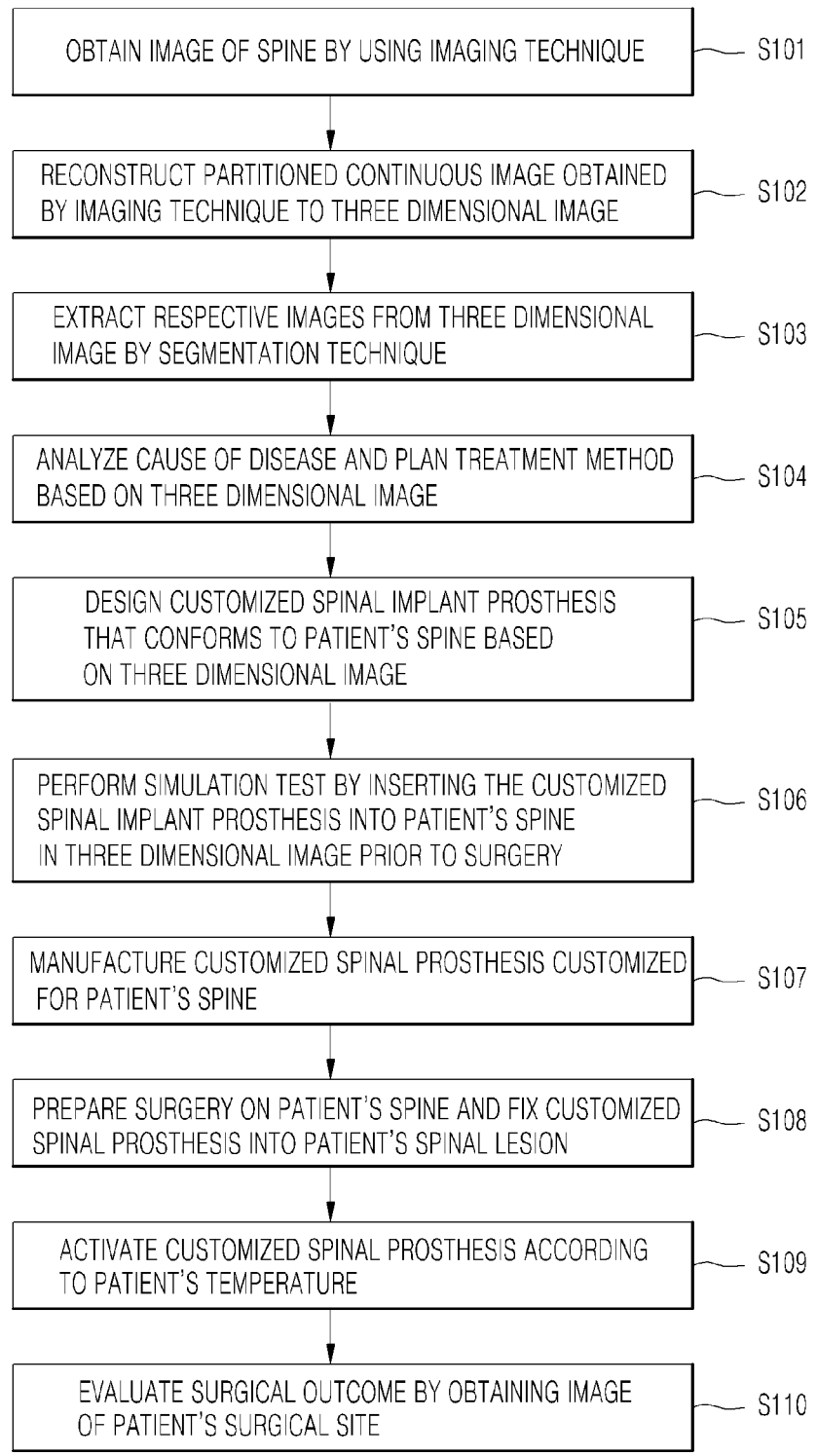
FIG. 2 is a block diagram illustrating an image-based, patient-specific spinal surgery according to the present invention.

FIG. 2 is a block diagram illustrating an image-based, patient-specific spinal surgery according to the present invention.

As shown, in an image-based, patient-specific medical spinal surgery method and a spinal prosthesis according to the present invention, in order to solve a problem that a spine 10 is damaged when mounting a spinal prosthesis 200 that has been used in a spinal surgery, the spinal prosthesis 200, which is tailored to a shape of the spine 10 of an individual patient, is manufactured in a polymer-based material for use in surgery by introducing an image of a patient.

In addition, in the image-based, patient-specific medical spinal surgery method, first, an imaging technique is used to obtain an image of the spine 10 of the patient (S101).

Here, the aforementioned imaging technique obtains the image of the patient's spine 10 by using one of a CT, an X-ray, or an MRI. Generally, the imaging technique is commonly used to diagnose a spinal disease, wherein the CT and the X-ray are commonly used as well as the MRI.

Generally, such image comprises a series of 2D slices images.

Also, a series of images of the patient's spine 10 obtained by the imaging technique is reconstructed into a three-dimensional image (S102).

That is, a two dimensional image obtained by scanning by the CT and the MRI is restored into the three dimensional high technical medical image, and specifically, a patient's lesion is scanned by the high technical CT and MRI and reconstructed into the three dimensional image to provide precise illustration.

Figure 3:
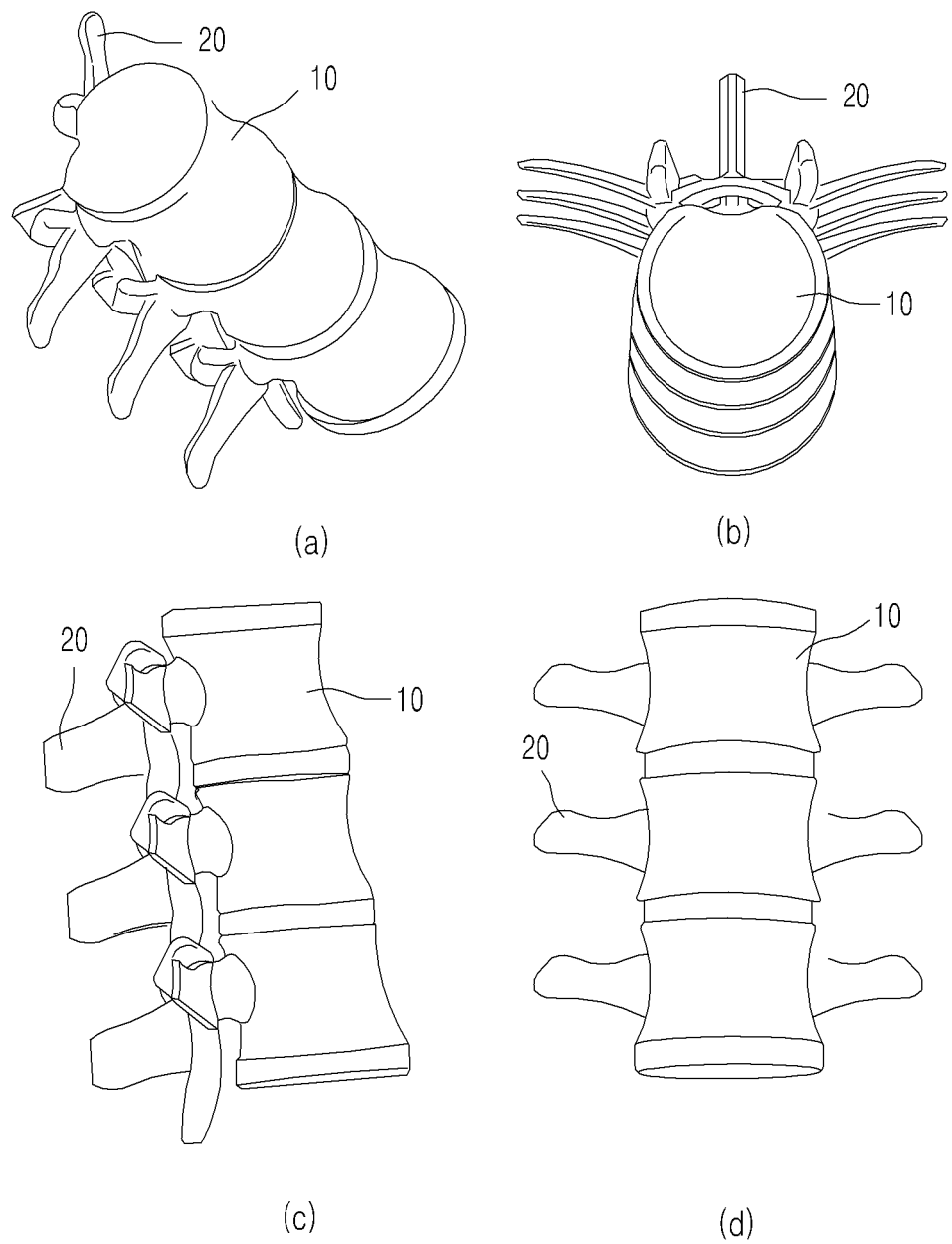
FIG. 3 is a view illustrating a patient's spine represented in three dimensions in an image-based, patient-specific spinal surgery according to the present invention.

Next, by using the series of 2D slice images of the patient's spine 10 obtained through the above imaging technique, the three dimensional image is reconstructed as shown in FIG. 3, and bones, muscles, nerves, and so forth are analyzed from the image obtained through the CT and the X-ray to extract an image of a particular spine 10 from an image of other tissues (bones, muscles, nerves, and so forth) by using a segmentation technique (S103).

Next, a cause of the lesion is analyzed and a treatment thereof is planned based on the segmented three-dimensional image (S104).

Based on the three dimensional image of the patient, an abnormal symptom of the spine 10 and a part that appears as a spinal deformity are exactly identified to determine a location in which the prosthesis is to be fixed.

In addition, when the location in which the prosthesis 200 is to be fixed is determined, the patient-specific spinal implant prosthesis 200 that conforms to the patient's spine 10 is designed by using the three dimensional image (S105).

By using the three dimensional image, the prosthesis 200 that conforms to the patient's spine 10 can be designed.

Here, after the customized spinal implant prosthesis 200 that conforms to the patient spine 10 is designed, a real prosthesis 200 is manufactured and a simulation test, in which the prosthesis 200 is inserted to the patient's spine 10 in the three dimensional image of the spine that conforms to the patient's spine 10 to be operated, is performed before performing a surgery (S106).

That is, by repeating the simulation in which the prosthesis 200 is inserted to the patient's spine 10 in the three dimensional image, which is designed to enable insertion of the prosthesis 200 into the vertebral process 20 based on the three dimensional image obtained by photographing the patient's spine 10, an error between a vertebral process 20 and an insert hole 210 of the prosthesis 200 is corrected, thereby testing the design of the prosthesis 200 that conforms to the vertebral process 20.

The prosthesis 200 designed according to the aforementioned design test method, is inserted to the three dimensional image of the spine to perform various simulations.

Through insertion of the implant prosthesis 200, a kinematic calibration part of the spine 10 is identified.

Also, through a hardness test of the implant prosthesis 200, it is determined whether the prosthesis 200 can endure a body's load (static load, dynamic load).

Also, through a simulation of thermal expansion, it is simulated what effect the implant prosthesis 200, which expands according to temperature, has to an entire structure.

Through these simulations, it is determined whether the designed implant is well designed.

If a result of the simulation indicates that the implant prosthesis 200 is not properly designed, designing the implant prosthesis 200 and performing the simulation are repeated.

Through repeating the process, the insert hole 210 of the prosthesis 200 that optimally conforms to the patient's spine 10 is produced.

In other words, the patient-specific implant prosthesis 200 that is designed to be insertable by using the three dimensional image has a reverse phase of the vertebral process 20 based on the image of the patient's spine such that the prosthesis 200 has a function of the implant as well as a structure preventing from dislocating after being inserted.

Next, the customized prosthesis 200 that conforms to the patient's spine 10 is manufactured (S107).

The prosthesis 200 has a structure preventing dislocating due to movement of the spine 10 and is manufactured into the implant prosthesis 200 by considering a load of the spine 10 and hardness of the implant 200.

Also, a bio-compatible polymer material is basically used for the prosthesis 200 and the prosthesis 200 is manufactured in a material which expands by human body temperature to be more tightly fixed.

In this case, an exemplary embodiment of the polymer that is used for manufacturing the prosthesis 200 is a hydrogel that is elastic and thus can provide the elastic restoring force.

The aforementioned prosthesis 200 may be manufactured in various methods, which includes a rapid prototyping method in which a variety of shapes are formed by directly using the polymer material to manufacture the prosthesis 200 and a molding method in which a shape of the implant prosthesis 200 is produced by using an RP polymer and then a mold of the implant prosthesis 200 is produced so that a desired prosthesis 200 in a biocompatible polymer may be produced.

In summary, the rapid prototyping (RP) method or the molding method are used for manufacturing the implant prosthesis 200 of which design is confirmed.

The rapid prototyping (RP) method manufactures the prosthesis 200 by stacking and processing various shapes using a CAD data of the given implant prosthesis 200 by directly using the polymer material.

Here, if a direct processing of a biocompatible polymer material is difficult, the shape of the implant prosthesis 200 may be produced by using a different RP polymer and then a molder may be produced using the shape of the implant prosthesis 200 and the implant prosthesis 200 in the biocompatible polymer material may be manufactured by using the molder according to the molding method. A shape of the implant prosthesis 200 that is manufactured in such a method may vary depending on a circumstance of the surgery.

When the prosthesis 200 that matches with the spine 10 is prepared, a surgery of patient's spine 10 to insert the implant prosthesis 200 to the patient's spine 10 is prepared, a patient's surgical incision is performed to provide an environment for inserting the implant prosthesis 200, and thereby a surgery for fixing the customized prosthesis 200 to the spinal lesion of the patient is performed (S108).

In other words, the manufactured implant prosthesis 200 is inserted to the lesion of the patient's spine 10 such that a hooking structure of the prosthesis 200 fixes securely the vertebral process 20 and presses till to be attached to other part of the spine securely. Next, the patient's incision is sutured.

In addition, the customized prosthesis 200 inserted to the vertebral process 20 of the patient's spine is activated by means of the body temperature (S109).

The prosthesis 200 that is inserted around the vertebral process 20 of the patient is stuck to the other spinal part closer by expanding due to the patient's body temperature and fixed thereto.

Finally, an image of the patient's spine 10 that is operated is obtained to identify an overall surgical outcome (S110).

Thus, the prosthesis 200 that is manufactured to match with the shape of the vertebral process 20 of the patient has an insertable structure such that a minimally invasive surgery may be provided.

Also, by using a simulation prior to manufacturing the prosthesis 200, a treatment effect of inserting the implant prosthesis 200 before/after the surgery may be estimated, and a surgery result may be identified through an image of the surgery.

The image-based, patient-specific spinal prosthesis according to an exemplary embodiment of the present invention described above is described with reference to FIG. 4.

Figure 4:
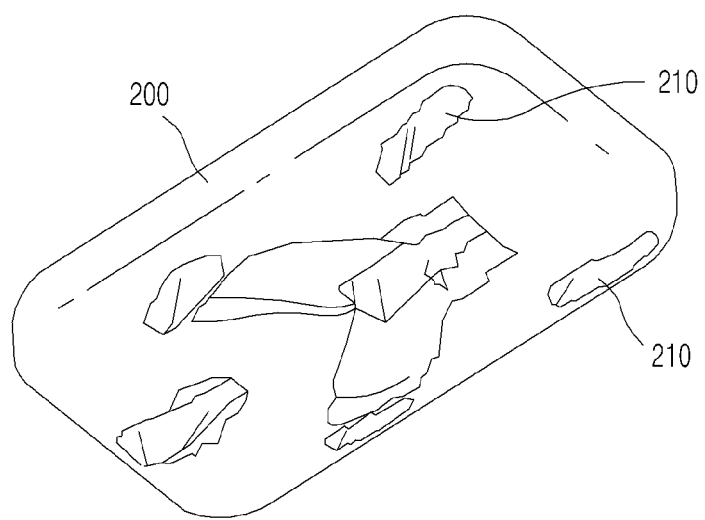
FIG. 4 is a view illustrating an image-based, patient-specific spinal prosthesis according to the present invention.
Figure 4:
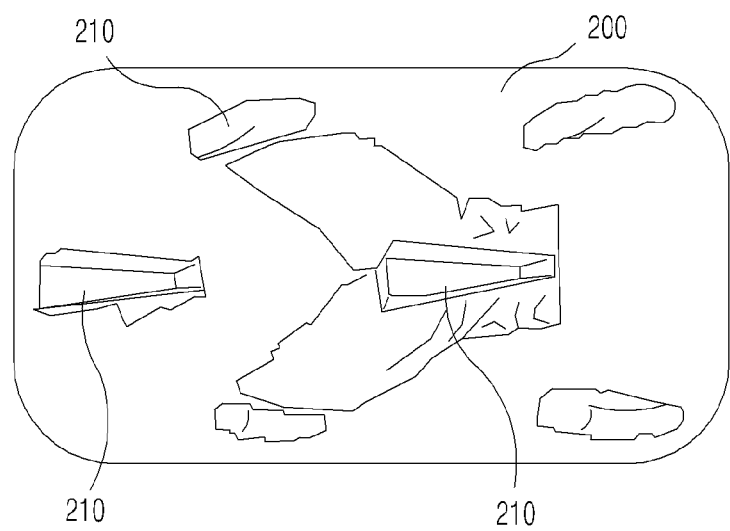

FIG. 4 is a view illustrating an image-based, patient-specific spinal prosthesis according to the present invention.

As shown in the drawing, in the image-based, patient-specific spinal surgery method and the spinal prosthesis, the prosthesis 200 that matches with the vertebral process 20 of the patient is manufactured by using the three dimensional image of the patient's spine 10 according to the imaging technique described above, as shown in FIG. 3.

The prosthesis 200 has a structure preventing dislocating due to movement of the spine 10 and is manufactured into the prosthesis 200 by considering a load of the spine 10 and hardness of the implant prosthetic 200.

Figure 5:
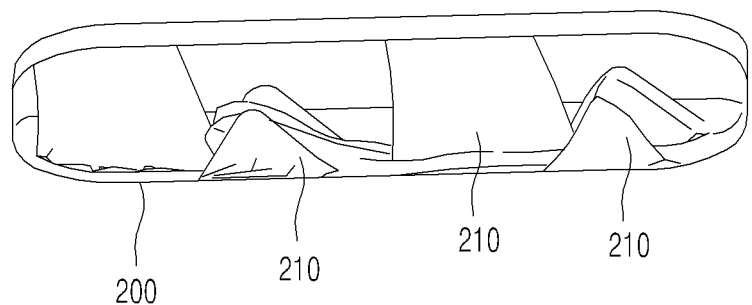
FIG. 5 is a cross sectional side view of an image-based, patient-specific spinal prosthesis according to the present invention.
Figure 5:
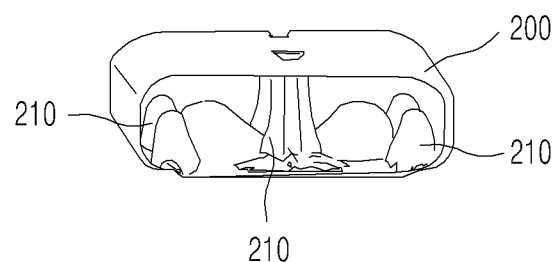

As shown in FIG. 5, the prosthesis 200 is manufactured to form the supporting insert hole 210 that has a predetermined shape corresponding to a size and a shape of the vertebral process 20 of the patient to be inserted.

In this case, in an example embodiment, the shape and the insert hole 210 of the prosthesis 200 are formed in conformity of the vertebral process 20, and a predetermined length and a width of the prosthesis 200 and the insert hole 210 may be formed differently according to the vertebral process 20 of the individual patient.

The prosthesis 200 has a predetermined thickness such that the prosthesis 200 having the predetermined thickness supports and connects the vertebral process 20 to each other.

In addition, a plurality of the vertebral processes 20 is contained in the insert hole 210 of the prosthesis 200 corresponding to the vertebral processes 20 to support between the vertebral processes 20 and provide variability, that is, the prosthesis being modifiable according to movement of the spine 10.

Figure 6:
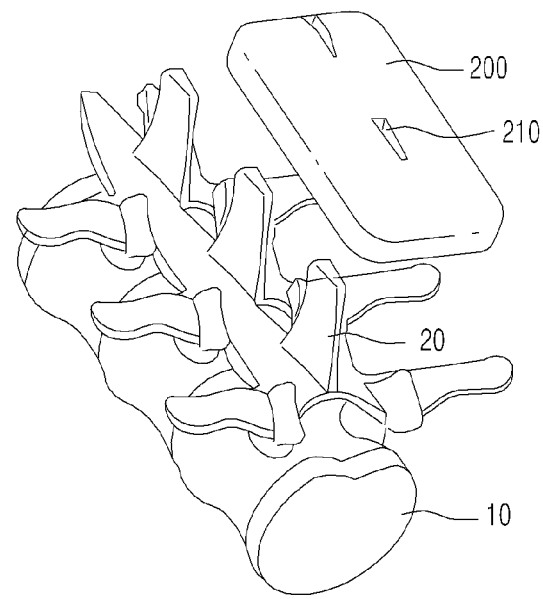
FIG. 6 is a view illustrating an image-based, patient-specific spinal prosthesis according to the present invention prior to being inserted to a spine.
Figure 6:
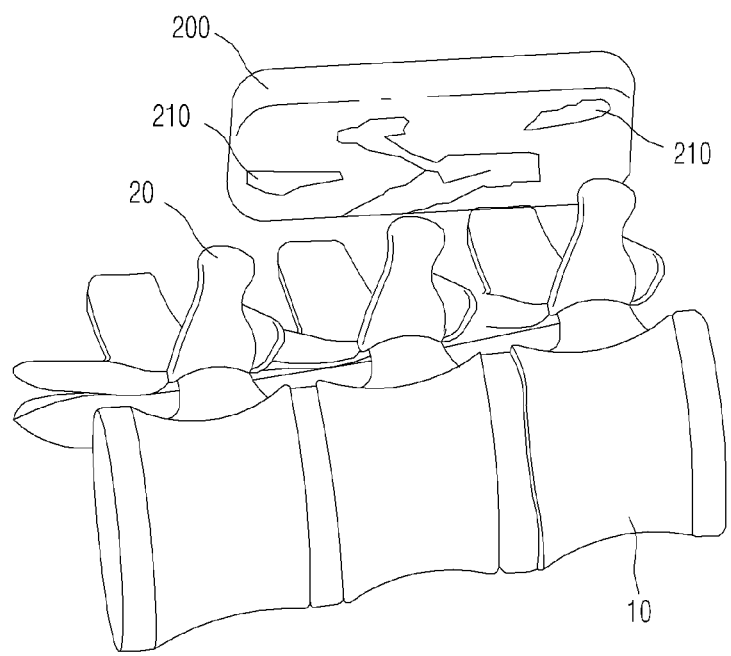
Figure 7:
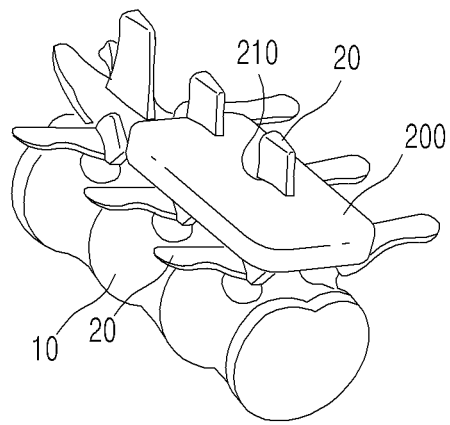
FIG. 7 is a view illustrating an image-based, patient-specific spinal prosthesis according to the present invention being inserted to and supported by a patient's spine.
Figure 7:
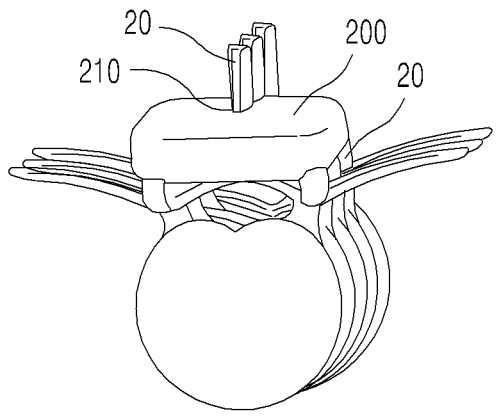
Figure 7:
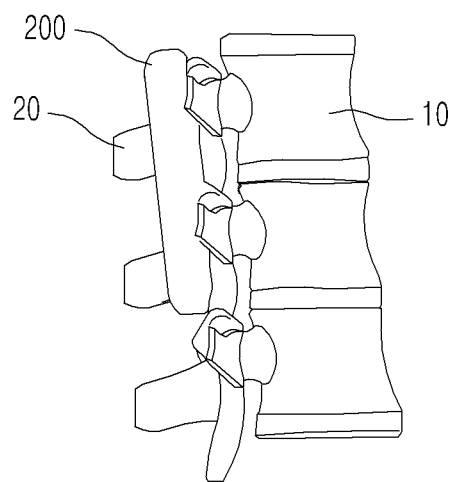
Figure 7:
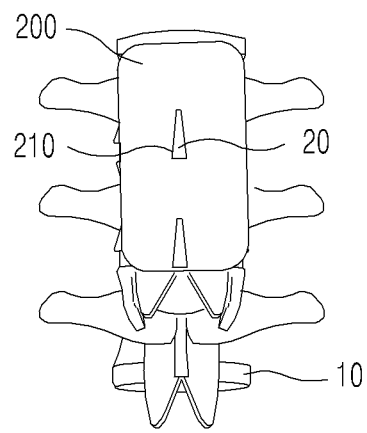

In other words, as shown in FIGS. 6 and 7, the prosthesis 200 is designed into an implant prosthesis customized for the patient's spine 10 that is insertable by using the three dimensional image in order to support and connect between the vertebral processes 20 of the patient, and to fixedly support the vertebral process 20 that is inserted to the insert hole 210.

Thus, the prosthesis 200 has a structure preventing from dislocating due to movement of the spine 10 and is manufactured by considering a load of the spine 10 and hardness of the prosthetic 200.

Here, the prosthesis 200 may be manufactured so that the insert hole 210 of the prosthesis 200 has the shape of the reverse phase with the vertebral process 20 of the patient, thereby enabling the prosthesis 200 to be inserted to the vertebral process 20 based on the three dimensional image obtained by photographing the spine 10 of the patient.

The bio-compatible polymer material may be used for the prosthesis 200 such that the prosthesis 200 expands by means of the human body temperature, thereby being more tightly fixed.

According to the image-based, patient-specific spine surgery method and the spinal prosthesis, the implant prosthesis 200 that is used in the spinal surgery is manufactured based on the image of the spine by using the imaging technique, thereby being customized for each individual patient, and has a structure in which the prosthesis 200 is insertable to the spine 10 without nailing the screw into the spine 10, thereby achieving a minimally invasive surgery.

In addition, in order to overcome a disadvantage that the existing implant is metallic, the prosthesis 200 based on the bio-compatible polymer is proposed so that the patient may have less repulsion thereto.

In the above, although the embodiments of the present invention have been described with reference to the accompanying drawings, a person skilled in the art should apprehend that the present invention can be embodied in other specific forms without departing from the technical spirit or essential characteristics thereof. Thus, the embodiments described above should be construed as exemplary in every aspect and not limiting.

The invention claimed is:

1. An image-based, patient-specific medical spinal prosthesis comprising:
   a prosthesis body on which a plurality of supporting insert holes are formed, each of the plurality of supporting insert holes having a predetermined shape corresponding to a size and a shape of a corresponding one of a plurality of vertebral processes of a patient in a surgical site, wherein each of the plurality of supporting insert holes of the prosthesis body is configured to receive the corresponding one of the plurality of vertebral processes to support between the plurality of vertebral processes, wherein the prosthesis body is modifiable according to a movement of a spine,
   wherein the prosthesis body is manufactured in a bio-compatible polymer material which undergoes thermal expansion that is activated by a body temperature of the patient, the prosthesis body thereby being more tightly fixed to the plurality of vertebral processes,
   wherein the prosthesis body includes a first side and a second side opposite to the first side, and the plurality of supporting insert holes includes, when taken from a sectional view of the prosthesis body, a blind hole that extends inwardly from the first side towards the second side but does not break through to the second side of the prosthesis body, and a through hole that extends through the prosthesis body from the first side to the second side, the through hole being configured to have the corresponding one of the plurality of vertebral processes enter the through hole from the first side, pass through the through hole, and protrude from the second side, wherein, when taken from a plan view viewed from the second side, the through hole is exposed to the second side and is entirely surrounded by the prosthesis body, wherein the prosthesis body is configured to be coupled to the plurality of vertebral processes only by the thermal expansion of the bio-compatible polymer material, and without a fastener for fixing the prosthesis body to the plurality of vertebral processes.

2. The image-based, patient-specific medical spinal prosthesis according to claim 1, wherein the prosthesis body is formed using a three dimensional image as an implant into which the plurality of vertebral processes are insertable, and the prosthesis body supports a region of the spine between respective ones of the plurality of vertebral processes of the patient and fixedly supports the corresponding one of the plurality of vertebral processes inserted into each of the plurality of supporting insert holes.

3. The image-based, patient-specific medical spinal prosthesis according to claim 2, wherein the prosthesis body has a structure preventing dislocation due to the movement of the spine and is manufactured by considering a load of the spine and a hardness of the implant.

4. The image-based, patient-specific medical spinal prosthesis according to claim 2, wherein each of the plurality of supporting insert holes of the prosthesis body is manufactured based on the three dimensional image obtained by imaging the spine of the patient such that the predetermined shape of each of the plurality of supporting insert holes is a reverse phase of the shape of the corresponding one of the plurality of vertebral processes of the patient such that each of the plurality of supporting insert holes of the prosthesis body is configured to receive the corresponding one of the plurality of vertebral processes.

5. The image-based, patient-specific medical spinal prosthesis according to claim 1, wherein:

the plurality of vertebral processes includes a first spinous process and a second spinous process;

the through hole receives the first spinous process and a second through hole receives the second spinous process;

the prosthesis body, taken from the plan view, includes a front side close to the through hole and a rear side opposite to the front side, and the first spinous process is disposed adjacent to a neighboring spinous process that is disposed outside the prosthesis body; and when the prosthesis body is coupled to the plurality of vertebral processes, the front side is spaced apart from the neighboring spinous process.

6. The image-based, patient-specific medical spinal prosthesis according to claim 5, wherein:

the plurality of vertebral processes further includes a first pair of articular processes corresponding to the first spinous process and a second pair of articular processes corresponding to the second spinous process;

and the blind hole is included in a first pair of blind holes receiving the first pair of articular processes and the plurality of supporting insert holes includes a second pair of blind holes receiving the second pair of articular processes.

* * * * *